(12) United States Patent
Schmidt et al.

(10) Patent No.: US 8,235,912 B2
(45) Date of Patent: Aug. 7, 2012

(54) SEGMENTING A CARDIAC ACOUSTIC SIGNAL

(75) Inventors: Samuel Emil Schmidt, Aalborg (DK); Johannes Jan Struijk, Terndrup (DK)

(73) Assignee: Acarix A/S, Kgs. Lyngby (DK)

( * ) Notice: Subject to any disclaimer, the term of this patent is extended or adjusted under 35 U.S.C. 154(b) by 198 days.

(21) Appl. No.: 12/726,364

(22) Filed: Mar. 18, 2010

(65) Prior Publication Data

US 2010/0249629 A1   Sep. 30, 2010

Related U.S. Application Data

(60) Provisional application No. 61/161,171, filed on Mar. 18, 2009.

(51) Int. Cl.
*A61B 7/04* (2006.01)
(52) U.S. Cl. ..................................................... 600/528
(58) Field of Classification Search .................. 607/28; 600/528
See application file for complete search history.

(56) References Cited

U.S. PATENT DOCUMENTS

2008/0013747 A1   1/2008   Tran

OTHER PUBLICATIONS

Schmidt, S.E.; Toft, E.; Holst-Hansen, C.; Graff, C.; Struijk, J.J.; , "Segmentation of heart sound recordings from an electronic stethoscope by a duration dependent Hidden-Markov Model," Computers in Cardiology, 2008 , vol., No., pp. 345-348, Sep. 14-17, 2008 doi: 10.1109/CIC.2008.4749049 URL: http://ieeexplore.ieee.org/stamp/stamp.jsp?tp=&arnumber.*
Reference Type: Book Chapter Author: Chung, Yong-Joo Primary Title: A Classification Approach for the Heart Sound Signals Using Hidden Markov Models Book Title: Structural, Syntactic, and Statistical Pattern Recognition Book Series Title: Lecture Notes in Computer Science Copyright: 2006 Publisher: Springer Berlin / Heidelberg.*
SE Schmidt, C Holst-Hansen, C Graff, E Toft, JJ Struijk, "Segmentation of heart sound recordings by a duration dependant hidden Markov model" Physiol. Meas. 31 (2010) 513-529. Published Mar. 5, 2010.*

* cited by examiner

*Primary Examiner* — Scott Getzow
*Assistant Examiner* — Amanda Patton
(74) *Attorney, Agent, or Firm* — Harness, Dickey & Pierce, P.L.C.

(57) ABSTRACT

The invention relates to segmentation of cardiac acoustic signals, such as the heart sound signal, based on statistical algorithms. A duration-dependent Hidden Markov Model is disclosed which models the shifting states of the heart, based on the cardiac acoustic signal and the time spent in the given states relating to physiological events, e.g. the various states of the heart during the heart beat cycle.

14 Claims, 4 Drawing Sheets

SEGMENTING A CARDIAC ACOUSTIC SIGNAL

The present application hereby claims priority under 35 U.S.C. §119(e) on U.S. patent application No. 61/161,171 filed Mar. 18, 2009, the entire contents of which is hereby incorporated herein by reference.

FIELD OF THE INVENTION

The invention relates to a method and apparatus for segmenting a cardiac acoustic signal, and in particular such methods and apparatuses being based on statistical algorithms.

BACKGROUND OF THE INVENTION

A simple, cheap and yet powerful assessment of the heart condition is an analysis of the heart sound by a trained doctor. From the mere sound, the trained doctor is capable of detecting whether or not the person has a healthy heart or a (potential) heart disorder. Computer-aided analysis (auscultation) of the heart offers new opportunities for broader application of this type of analysis in situations when the trained doctor is not present. Moreover, computer-aided analysis of the heart sound may extend the application to situations which otherwise would require more advanced analysis as well as to situations where a diagnosis may be based on the heart sound.

Several method for computer-aided auscultation of heart sounds have been proposed in order to provide quantitative, accurate and objective interpretation of the heart sounds. An example of such a method is provided in the published US patent application 2008/0013747 A1 which discloses an electronic stethoscope capable of automatic auscultation of the cardiovascular system. Embodiments are disclosed where the timing of characteristic heart sound features are extracted from a correlation between the heart sound and an ECG signal using an analysis that may be based on Hidden Markov Models and semi-Hidden Markov Models. In the disclosed method both the heart sound and the ECG signal are needed in order to extract the timing of heart sound features.

An important step in computer-aided auscultation of heart sounds is segmentation of the heart sound. Identifying the states in the heart cycle, such as the diastolic and systolic periods is fundamental in almost all heart sound algorithms. The first heart sound (S1) and the second heart sound (S2) are the dominating audible reflections, and indicates the beginning of the systole and the diastole, respectively.

Detection of S1 and S2 is complicated by background noise, variations in heart rhythm, anatomical variations, different recording sites, recording artefacts and pathological heart sounds. Segmentation of heart sounds recorded with handheld stethoscopes in clinical settings are especially challenging due to background noise and friction noise between the stethoscope and the skin.

SUMMARY OF THE INVENTION

The inventors of the present invention have realized that while Hidden Markov Models (HMM) is well suited since it assumes a double stochastic process, it does not model the duration of the states explicitly. Instead, the inventors of the present invention have realized that a duration-dependent hidden Markov Model (DHMM) could be used as the underlying model of segmentation of a heart sound.

Accordingly, in a first aspect there is provided a method of segmenting a cardiac acoustic signal, the method comprising:

obtaining a cardiac acoustic signal; and
segmenting the cardiac acoustic signal into time intervals related to physiological events;
wherein the segmenting of the cardiac acoustic signal is based on a duration-dependent Hidden Markov Model analysis of the cardiac acoustic signal.

A DHMM is thereby obtained which models the shifting states of the heart, based on the cardiac acoustic signal and the time spent in the given states relating to the physiological events. In a standard HMM, the shifting states of the heart is modelled based on the cardiac acoustic signal and the known sequence of the heart cycle. In the DHMM, in accordance with the present invention, also the state duration of the physiological events of the heart cycle is included, thereby incorporating the periodicity of the heart cycle. In embodiments, the physiological events are the various states of the heart during the heart beat cycle. This is e.g. advantageous for discriminating noise peaks from peaks relating to a physiological event of the heart cycle. Moreover, embodiments of the present invention are advantageous, since they allow segmenting the cardiac acoustic signal based on the cardiac acoustic signal alone, and not correlated with other signals.

Studies based on algorithm implementations of embodiments of the present invention have shown that it is possible to reliably segment patient cardiac heart sound recordings with a high precision, even though the recordings were contaminated with background noise and noise from the recording process, such as friction noise.

In general, a duration-dependent hidden Markov Model may also be referred to as a modified hidden Markov Model or semi-hidden Markov Model.

The present invention may advantageously be implemented in computer-aided auscultation algorithms. Both in connection with apparatuses for segmenting a cardiac acoustic signal, such as electronic stethoscopes and on computer-readable media having stored therein instructions for causing a processing unit to execute embodiments of the present invention.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

The present invention is based on a Hidden Markov model (HMM) type modelling of physiological events of the heart cycle. In embodiments, the physiological events are various states of the heart during the heart beat cycle. In embodiments the physiological events are the first heart sound state (S1), the silent systole state (siSys), the second heart sound (S2) and the silent diastole (siDia).

Figure 1:
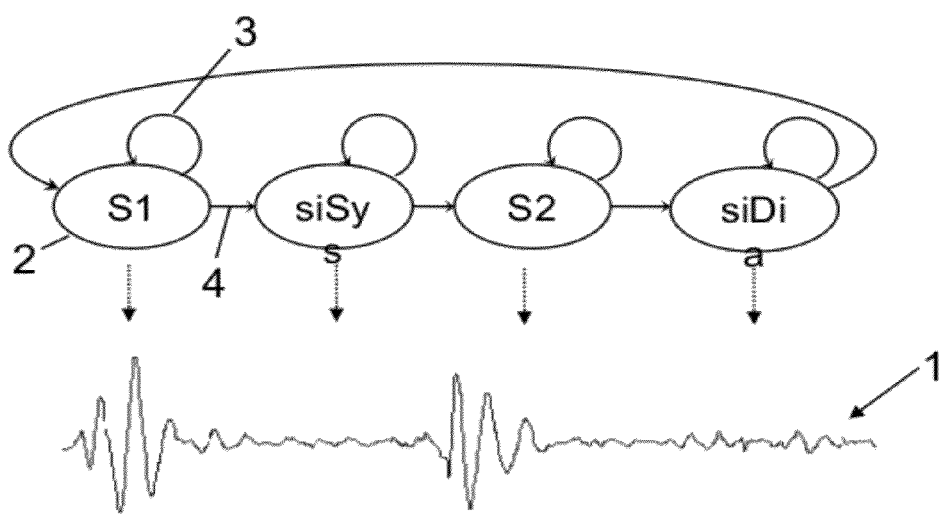
FIG. 1 shows a schematic illustration of a Hidden Markov model of the heart cycle.

FIG. 1 shows a schematic illustration of a Hidden Markov model of the heart cycle. The observables are the heart sound signal 1 with the associated Hidden Markov model where state and transition probabilities have been assigned to the states being in the first heart sound state S1, 2, remaining in the first heart sound state 3 and transition to the silent systole state siSys, 4. Similar assignments have been made for the other three states: the silent systole (siSys), the second heart sound (S2) and the silent diastole (siDia).

In the HMM, the known sequence of the heart cycles is used, so that the transition sequence probabilities are set as follows:
S1: set to 1 for the transition S1→siSys and zero otherwise;
S2: set to 1 for the transition S2→siDia and zero otherwise;
siSys: set to 1 for the transition siSys→S2 and zero otherwise;
siDia: set to 1 for the transition siDia→S1 and zero otherwise.

Thus the HMM is constraint to follow the known sequence of the heart cycle: S1→siSys→S2→siDia siDia→S1. Thus a non-ergodic Markov Model is applied.

In a standard HMM the probability of either remaining in a given state 3 or make the transition to the next state 4 is constant in the sense that it depends only on the detected signal 1 and not on the time spend in the state.

In the present invention, in addition to constraining the transition sequence in the HMM, the state probability is modulated by the time spent in a given state, thus a duration-dependent Hidden Markov Model (DHMM) is applied in order to analyze the heart sound signal 1. The DHMM thus models a state duration of the physiological events of the heart cycle.

Figure 2:
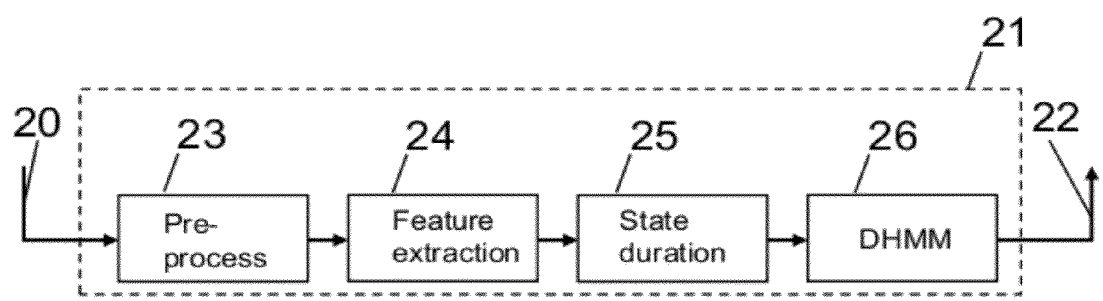
FIG. 2 illustrates a schematic embodiment of aspects relating to the DHMM-analysis of the heart signal.

FIG. 2 illustrates a schematic embodiment of aspects relating to the DHMM-analysis of the heart signal.

In embodiments various steps may be applied, however in the broadest aspect of the present invention a cardiac acoustic signal 20, i.e. a heart sound is obtained and based on a duration-dependent Hidden Markov Model (DHMM) analysis 21 of the cardiac acoustic signal, the cardiac acoustic signal is segmented 22 into at least one of the two states S1 and S2 and optionally or additionally also into the other two states siSys and siDia. The segmenting reflects the most probable timing of the sequence of segments of the heart sound.

In embodiments of the present invention the state duration is defined by use of a predefined probability distribution. The probability distribution may typically be a normal distribution for the standard patients. However, for special patients, such as patients with strong arrhytmia or heart valve diseases, other types of probability distributions may be selected. For example, for a patient with arrhytmia where the duration of the diastole is completely random, a uniform probability distribution may be selected, or a custom-defined probability distribution specifically related to arrhytmia may be applied.

Figure 3:
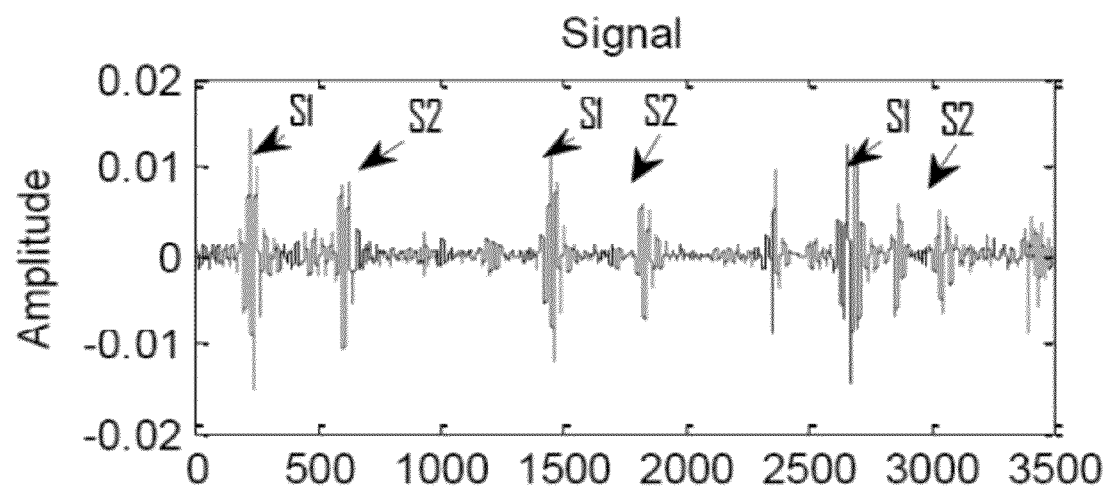
FIG. 3 shows a graph of a heart sound signal.

FIG. 3 shows a graph of a heart sound signal with assignments of S1 and S2 indicated. In order to extract the features relating to the heart sounds a number of processing steps may be applied to the sound signal. An implementation of a given set of processing steps is illustrated in FIG. 2 as indicated be reference numeral 21.

Prior to or as a step of the segmenting process of the cardiac acoustic signal, the cardiac acoustic signal is pre-processed 23. Different pre-processing routines may be applied singly or in combination. In an embodiment, the following pre-processing is used.

In a first part of the pre-processing the signal is band-pass filtered to remove sound with frequencies below a low threshold, e.g. 25 Hz and above a high threshold, e.g. 400 Hz. In a 10 second part of the pre-processing noisy spikes are removed, e.g. by using an identification routine and substitute noise parts with constant parts, such as a zero signal. Also signal parts with exceptional high amplitudes may be removed to reduce influence from background noise.

Figure 4:
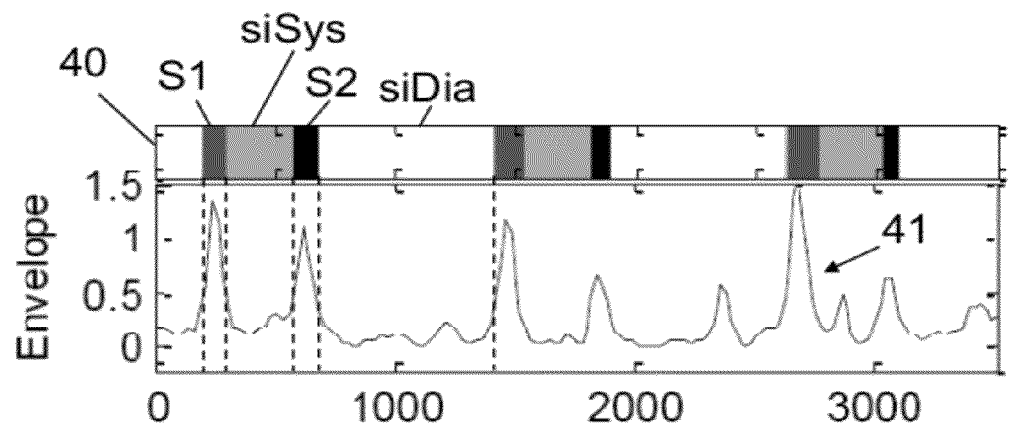
FIG. 4 illustrates an envelogram of the sound signal of FIG. 3.

Moreover, the pre-processing may include, or a separate step may be provided which includes, a step of processing the sound signal to an envelope signal. In an embodiment, the signal was processed into a homomorphic envelogram. FIG. 4 illustrates a homomorphic envelogram 41 of the sound signal of FIG. 3. Moreover, the envelope was normalized with the 97th percentile value of the envelope to reduce the inter-patient variation. The 97th percentile value is used as reference value since it is robust to high amplitude noise spikes.

Figure 6:
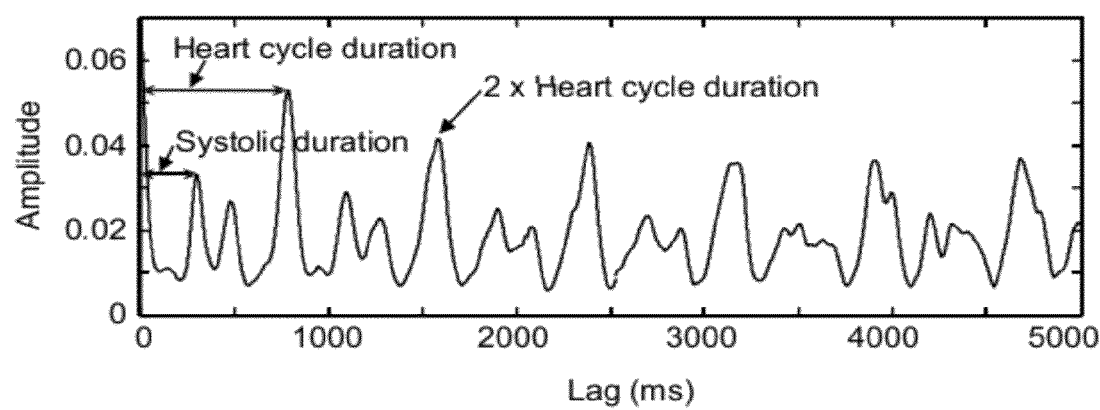
FIG. 6 illustrates a graph of the envelope auto-correlation.

Signal feature and parameter values (FIG. 2, 24) may be estimated by use of statistics from a training dataset where the true states are known to define global properties which apply to all recordings. Analysis of data has shown that inter-subject variation in mean and variance of the envelope signal of distribution and duration of S1 and S2 were small and fixed values may be used for these values. However the duration of the systole and the diastole is observed to vary significant from subject to subject and as a consequence the distribution parameters for the durations of the systole and the diastole were estimated individually for each subject. In an embodiment, the envelope signal is auto-correlated in order to extract timing information of signal features, i.e. to extract durations of the systole and the diastole (FIG. 2, 25). In the autocorrelation, the distance from lag null to the first distinct peaks reflects the durations of the systole and diastole. The estimation of the state durations from the envelope auto-correlation is illustrated in FIG. 6.

Having collected and/or estimated the various parameters to be used in the DHMM, the segmentation can be performed (FIG. 2, 26) in order to assign states to the various segments of the sound signal. Further details of the DHMM process are provided below.

FIG. 4 illustrates an example of an output of the segmentation process. FIG. 4 shows the envelogram 41 of the sound signal, and on top of this, a segment assignment 40 is shown indicated the beginning, duration and end of the four states.

The cardiac acoustic signal may in an embodiment be obtained in real-time and concurrently with obtaining the acoustic signal, the segmenting is performed also in real-time, possibly with a delay from the processing. Real-time segmentation may be performed in connection with an implementation in such an apparatus as an electronic or digital stethoscope. A digital stethoscope comprises an input unit for receiving the cardiac acoustic signal, typically in the form of a microphone to be attached to the skin of the person, as well as a processing unit.

In an alternative embodiment, the segmentation is performed on a pre-recorded cardiac acoustic signal. The cardiac acoustic signal may be recorded by an electronic or digital stethoscope or by other means for recording a cardiac acoustic signal. The segmentation may then be performed in such an apparatus as a computer properly programmed to execute the method in accordance with embodiments of the present invention.

Description of Hidden Markov Models

In the following, further mathematical details are given in connection with the mathematical description of the duration dependent Hidden Markov model in accordance with embodiments of the present invention.

Central in the standard Markov model is the transition probabilities $a_{ij}$ which defines the probability of state j at next time instances given state i at the current time instance.

$$a_{ij} = P(q_{t+1} = S_j | q_t = S_i) \quad (Eq. 1)$$

where $q_t$ is the time-state vector defining the states at time t, S denotes the individual states as $S = \{S_1, S_2 \ldots, S_N\}$, which in the current implantation corresponds to $S = \{siSys, siDia, S1, S2\}$. However, Eq. 1 is a limited model of the cardiac cycle since the probability of transition is not independent of the time spend in a given state. For example the probability of transition from diastole to S1 is more likely in the end of the diastolic period than in the beginning. In the duration dependent Markov model the transition probability is supplemented with a duration probability distribution for each state $p_j(d)$.

In the HMM and DHMM the true states: $Q = \{q_1, q_2, \ldots q_t\}$ are not known, the Markov model is hidden, but an observation sequence O is known. In FIG. 4 the observation sequence O is the envelope of the cardiac acoustic signal 41. The observation is related to the states with the observation probability distribution: $B = \{b_j(O_t)\}$, which defines the probability that state "j" generates the output $O_t$. The task is to estimate the state sequence which is most likely to produce the given observations:

$$Q^* = \mathrm{argmax}_Q P(Q | O, \lambda) \quad (Eq. 2)$$

where Q* is the state sequence of all possible state sequences which is most likely to produce O. Lambda ($\lambda$) denotes the model parameters such as the transition matrix, observation probability distribution and in the case of the DHMM, the duration distribution. Solution of Eq. 2 requires calculation of all combinations of Q, which can be shown to correspond to $T*N^T$ multiplications were T is the number of samples and N the number of states. Therefore the DHMM is implemented as a forward algorithm calculating an estimated instantaneous probability $\delta_t(j)$ of $q_t$ changing to a new state at the next time instant.

$$\delta_t(j) = P(O_1, O_2, \ldots O_t, q_t = S_j, q_{t+1} \neq S_j | \lambda) \quad (Eq. 3)$$

Given the duration d and that the previous state was i at time $t - d_j$, the forward calculated probability that $q_t$ is the last time instance in state j is calculated as $$\delta_t(j, i, d) = \delta_{t-d}(i) a_{ij} p_j(d) \prod_{s=0}^{d-1} b_j(O_{t-s}) \quad (Eq. 4)$$

where $p_j(d)$ is the density distribution of the state duration, $\delta_{t-d}(i)$ is the probability that the previous state i ended at t−d, and $a_{ij}$ is the transition probability when a transition to a new state occurs. The expression to the right of the product sign in Eq. 4 is the probability that the state j generated the output observed in the period t−d to t. From Eq. 4 $\delta_t(j)$ is estimated by maximizing according to both the duration d and the previous state i.

$$\delta_t(j) \approx \max_d \max_{i \neq j} \left[ \delta_{t-d}(i) a_{ij} p_j(d) \prod_{s=0}^{d-1} b_j(O_{t-s}) \right] \quad (Eq\ 5)$$

The d and i which maximized (Eq. 4) is stored and later used in a backtracking algorithm. The q* is found by backtracking though the stored values of d and i. By maximizing in d the duration dependence of the of the states i is dealt with.

Performance

The performance of the DHMM segmentation was studied based on a selected population of patients referred for coronary arterial angiography. The performance of the DHMM segmentation in accordance with embodiments of the present invention was compared to a standard HMM, with both models using the same envelope as input. The ability of both models to locate S1 and S2 correctly was measured by sensitivity and positive predictive value for 73 test recordings. A sound was correctly located if the center of the detected sound was closer than 60 ms to the center of a similarly predefined sound. All other detected sounds were defined as false positives. Since the models need a short time period in the beginning and end of the recordings to overcome end effects, the first, the second and the last 1.5 seconds of the recordings were excluded from the sensitivity and positive predictive value test. A Wilson interval was used to define the 95% confidence intervals (CI) of sensitivity and positive predictive values.

In the 73 recordings that were included in the test, the DHMM model identified 890 S1 and S2 sounds out of 901 which corresponded to a sensitivity of 98.8% (CI: 97.8-99.3%) see table 1. In 66 recordings out of 73 recordings no sounds were missed.

TABLE 1

| Models | Sensitivity | Positive predictive value |
| --- | --- | --- |
| DHMM | 98.8% (CI: 97.8-99.3%) | 98.6% (97.6-99.1%) |
| HMM | 59.9% (CI: 56.7-63.1%) | 54.8% (CI: 51.6-58%) |

The DHMM misplaced 13 sounds more than 60 ms, which corresponds to 98.6% (97.6-99.1%) positive predictive value. The standard HMM had a sensitivity of 59.9% (CI: 56.7-63.1%) and positive predictive value of 54.8% (CI: 51.6-58%), which was considerably lower than the DHMM. A typical error for the HMM was confusion between noise spikes and S1 and S2 sounds.

Figure 5:
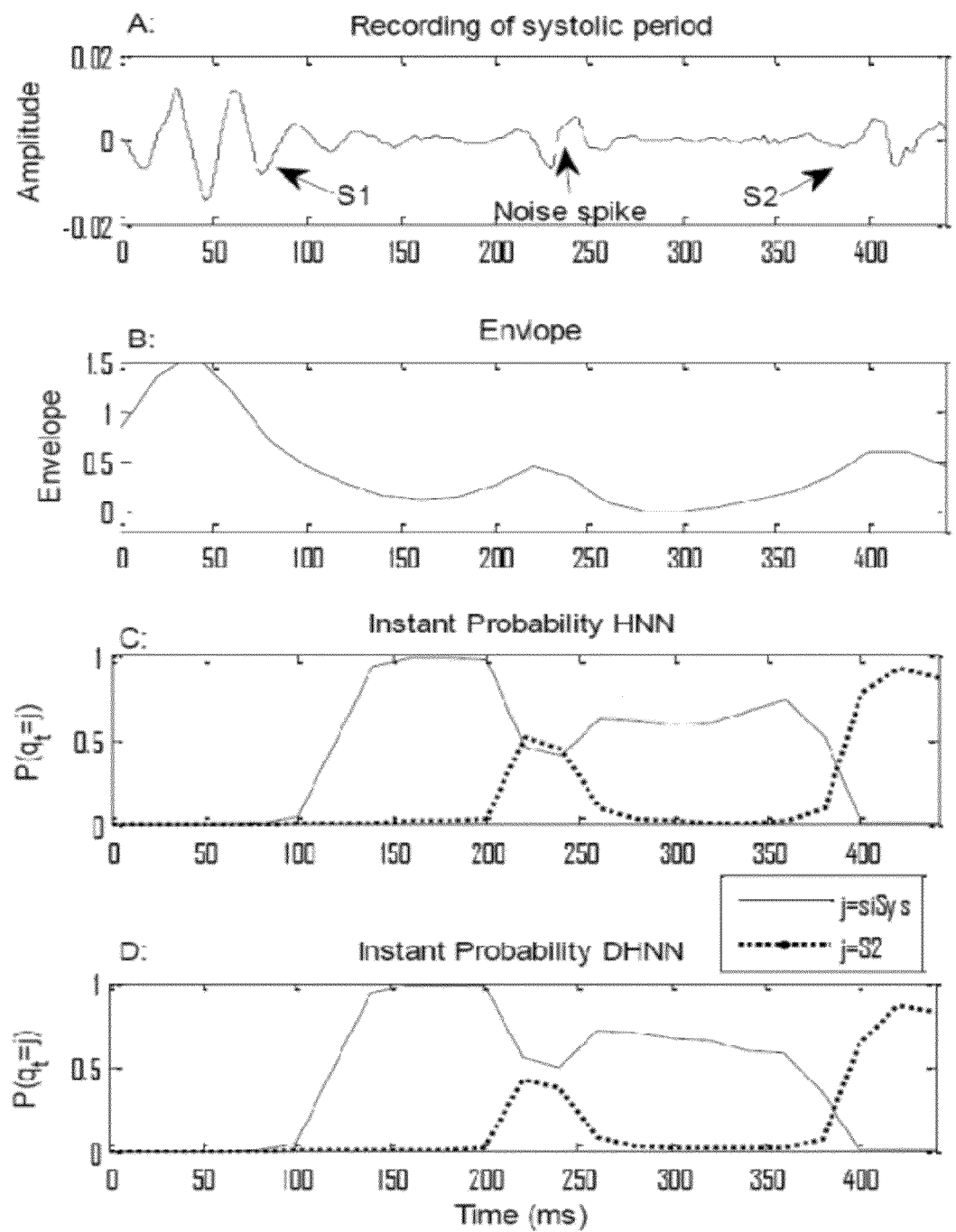
FIG. 5 illustrates a comparison between the DHMM and the HMM over a systolic period.

The improvement of DHMM over HMM is illustrated in FIG. 5 over a systolic period. In FIG. 5A a systolic period bounded by S1 and S2 and contaminated by a noise spike is shown. FIG. 5B illustrates the signal envelope, whereas FIG. 5C illustrates the probability that $q_t$ is in state siSys or state S2 calculated with a forward HMM algorithm as used in the prior art methods. The noise spike at 220 ms erroneously makes the probability of S2 higher than siSys. FIG. 5D is similar to FIG. 5C but with the probability calculated using DHMM in accordance with the embodiments of the present invention, which reduces the effect of the noise spike, and now correctly makes the probability of S2 lower than siSys.

It has thus been shown that the DHMM is well suited for segmenting heart sounds recorded at bedside with a commercially available electronic stethoscope. Consistent and reliable segmentation can be achieved without the use of other signals as the ECG. A high precision may be obtained even though recordings were contaminated with background noise and noise from the recording process such as friction noise. Moreover, the DHMM outperformed the standard HMM The invention can be implemented in any suitable form including hardware, software, firmware or any combination of these. The invention or some features of the invention can be implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A method of segmenting a cardiac acoustic signal, the method comprising:
   obtaining the cardiac acoustic signal, the cardiac acoustic signal including at least one cardiac cycle with a plurality of states;
   analyzing the cardiac acoustic signal by applying a Hidden Markov Model that takes into consideration a duration of each of the plurality of states; and
   temporally segmenting the cardiac acoustic signal into a plurality of intervals, each of the plurality intervals being associated with a corresponding state of the plurality of states,
   wherein a length of each of the intervals is determined using the Hidden Markov Model that takes into consideration a duration of the corresponding state with which each of the plurality of intervals is associated.

2. The method according to claim 1, wherein the Hidden Markov Model models a duration of state of the plurality of states of the at least one cardiac cycle.

3. The method according to claim 2, wherein the duration of state is defined by a probability distribution.

4. The method according to claim 1, wherein the segmenting of the cardiac acoustic signal is a segmenting into segments related at least to first (S1) and second (S2) heart sounds.

5. The method according to claim 1, wherein the Hidden Markov Model assumes a cyclical sequence of states with the following transition pattern: S1-state→silent systole (siSys) state→S2-state→silent diastole (siDia) state→S1-state.

6. The method according to claim 1, wherein the segmenting of the cardiac acoustic signal reflects a most probable timing of a sequence of segments related at least to first (S1) and second (S2) heart sounds given the cardiac acoustic signal.

7. The method according to claim 1, wherein prior to segmenting the cardiac acoustic signal, the cardiac acoustic signal is pre-processed.

8. The method according to claim 1, wherein prior to segmenting the cardiac acoustic signal, the cardiac acoustic signal is processed to an envelope signal.

9. The method according to claim 8, wherein the cardiac acoustic signal or the envelope signal is auto-correlated to extract the duration of each of the plurality of states.

10. The method according to claim 8, wherein a probability distribution of a duration of state is estimated from the duration of each of the plurality of states extracted using auto-correlation.

11. The method according to claim 1, wherein the cardiac acoustic signal is obtained in real-time, and the segmenting is performed in real-time.

12. The method according to claim 1, wherein the segmenting of the cardiac acoustic signal is performed on a pre-recorded cardiac acoustic signal.

13. An apparatus for segmenting a cardiac acoustic signal, the apparatus comprising:
   an input unit configured to receive the cardiac acoustic signal, the cardiac acoustic signal including at least one cardiac cycle with a plurality of states; and
   a processing unit adapted to,
      analyze the cardiac acoustic signal by applying a Hidden Markov Model that takes into consideration a duration of each of the plurality of states, and
      temporally segment the cardiac acoustic signal into a plurality of intervals, each of the plurality intervals being associated with a corresponding state of the plurality of states,
   wherein a length of each of the intervals is determined using the Hidden Markov Model that takes into consideration a duration of the corresponding state with which each of the plurality of intervals is associated.

14. A computer-readable medium having stored therein instructions that cause a processing unit to execute the method according to claim 1.

* * * * *